(12) United States Patent
Tanaka (10) Patent No.: US 11,162,006 B2
(45) Date of Patent: Nov. 2, 2021

(54) WATER-RICH ADHERENT GEL, COMPOSITION FOR MANUFACTURING WATER-RICH ADHERENT GEL, AND ELECTRODE PAD

(71) Applicant: SEKISUI PLASTICS CO., LTD., Osaka (JP)

(72) Inventor: Hiroyoshi Tanaka, Ibaraki (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 1114 days.

(21) Appl. No.: 15/124,878

(22) PCT Filed: Mar. 20, 2015

(86) PCT No.: PCT/JP2015/058517
§ 371 (c)(1),
(2) Date: Sep. 9, 2016

(87) PCT Pub. No.: WO2015/146840
PCT Pub. Date: Oct. 1, 2015

(65) Prior Publication Data
US 2017/0015881 A1   Jan. 19, 2017

(30) Foreign Application Priority Data
Mar. 28, 2014   (JP) .............................. JP2014-069702

(51) Int. Cl.
*C09J 133/26* (2006.01)
*A61B 18/16* (2006.01)
(Continued)

(52) U.S. Cl.
CPC .......... *C09J 133/26* (2013.01); *A61B 18/1402* (2013.01); *A61B 18/16* (2013.01);
(Continued)

(58) Field of Classification Search
CPC .......... C09J 133/26; C09J 11/06; C09J 11/04; A61B 18/16; A61B 18/1402;
(Continued)

(56) References Cited

U.S. PATENT DOCUMENTS 5,922,764 A * 7/1999 Cantin .................. A61K 8/042
514/557
2002/0018958 A1* 2/2002 Nishioka ................... B41C 1/05
430/260
(Continued)

FOREIGN PATENT DOCUMENTS

EP    1739149 A1    3/2007
JP    S61-022839 A   1/1986
(Continued)

OTHER PUBLICATIONS

International Search Report issued with respect to Application No. PCT/JP2015/058517, dated Jun. 9, 2015.
(Continued)

*Primary Examiner* — Alexander C Kollias
(74) *Attorney, Agent, or Firm* — Greenblum & Bernstein, P.L.C.

(57) ABSTRACT

The present invention provides an adhesive, high water content gel that does not cause a heat generation problem even when used as a patient plate for electrosurgical units through which high current flows and that is excellent in adhesion, as well as an electrode pad including the gel. The present invention relates to an adhesive, high water content hydrogel containing a polymer matrix that includes a copolymer of a polymerizable monomer and a crosslinkable monomer, water, a polyhydric alcohol, an electrolyte, polyacrylic acid, and polyvinyl alcohol, the hydrogel containing, based on 100% by weight of the total hydrogel, 40-70% by weight of water, 1.0-5.0% by weight of polyacrylic acid, and 0.5-5.0% by weight of polyvinyl alcohol, and being pro-
(Continued)

duced by copolymerization. An electrode pad is also obtained by coating a conductive layer formed on a base film with the adhesive, high water content hydrogel.

12 Claims, 1 Drawing Sheet (51) Int. Cl.
  *A61B 18/14* (2006.01)
  *A61L 24/00* (2006.01)
  *A61L 24/04* (2006.01)
  *C09J 11/04* (2006.01)
  *C09J 11/06* (2006.01)
  *A61B 18/00* (2006.01)
(52) U.S. Cl.
  CPC ......... *A61L 24/0031* (2013.01); *A61L 24/043* (2013.01); *C09J 11/04* (2013.01); *C09J 11/06* (2013.01); *A61B 2018/00077* (2013.01); *A61B 2018/00589* (2013.01)
(58) Field of Classification Search
  CPC ........... A61B 2018/00589; A61B 2018/00077; A61L 24/043; A61L 24/0031
  See application file for complete search history.

(56) References Cited

U.S. PATENT DOCUMENTS

2005/0271725 A1* 12/2005 Kuribayashi ........ A61K 9/0014
  424/486
2007/0009582 A1* 1/2007 Madsen ................ A61L 15/585
  424/445
2007/0020325 A1* 1/2007 Kuribayashi .......... A61K 47/02
  424/448
2007/0208130 A1* 9/2007 Sasahara ................ A61B 5/259
  524/521
2013/0289157 A1* 10/2013 Sato ....................... C09J 133/02
  523/105

FOREIGN PATENT DOCUMENTS

| JP | S61-023670 A | 2/1986 | |
| JP | S61-268767 A | 11/1986 | |
| JP | S62-270135 A | 11/1987 | |
| JP | H02-080030 A | 3/1990 | |
| JP | H03-267041 A | 11/1991 | |
| JP | 2003-346554 A | 5/2003 | |
| JP | 2003-250913 A | 9/2003 | |
| JP | 2005-097408 A | 9/2003 | |
| JP | 3714982 B2 | 11/2005 | |
| JP | 4522405 B2 | 8/2010 | |
| JP | 2012-197344 A | 3/2011 | |
| JP | 2004-292592 A | 10/2012 | |
| WO | WO-2012093505 | * 7/2012 | ............ C09J 133/02 |
| WO | 2013/039151 A1 | 3/2013 | |

OTHER PUBLICATIONS

International Preliminary Report on Patentability issued with respect to Application No. PCT/JP2015/058517, dated Oct. 4, 2016.

* cited by examiner

WATER-RICH ADHERENT GEL, COMPOSITION FOR MANUFACTURING WATER-RICH ADHERENT GEL, AND ELECTRODE PAD

TECHNICAL FIELD

The present invention relates to an adhesive, high water content hydrogel that is suitable as an adhesive gel to be attached to a living body for its use, such as for use in electrocardiographic electrodes or terminals of electrotherapeutic apparatuses, and particularly to an adhesive, high water content hydrogel that is less likely to generate heat even when high current flows therethrough, such as for use in patient plates of electrosurgical units. The present invention also relates to a method for producing the adhesive, high water content hydrogel, an electrode pad including the adhesive, high water content hydrogel, and a composition for producing the adhesive, high water content hydrogel.

BACKGROUND ART

High-frequency therapeutic apparatuses and electrosurgical units are examples of therapeutic apparatuses using high-frequency current. High-frequency therapeutic apparatuses achieve the effects of relief of muscle fatigue or rehabilitation by allowing a stimulating current to flow through a living body from an electrode pad adhered to the living body. Electrosurgical units are widely used in surgeries and achieve the effects of cutting or coagulating body tissues around a probe by bringing the probe close to a living body adhered to an electrode pad (patient plate), and allowing a high-frequency current to flow between the probe and the electrode pad.

JP 3714982 B (Patent Literature 1) discloses an example of an electrode pad for use in electrosurgical units, among the above-mentioned apparatuses.

CITATION LIST

Patent Literature

Patent Literature 1: JP 3714982 B

SUMMARY OF INVENTION

Technical Problem

When conventional electrosurgical units are used, since a current is allowed to flow through a narrow part and is then collected at an electrode pad which serves as a patient plate with a large area, the current density is low at the patient plate. However, a mode has been available in recent years which denatures proteins to surely cause thermal coagulation without carbonizing tissues. In this mode, a current is allowed to flow relatively broadly, and it is therefore pointed out that low-temperature burns may be caused because the current density at the patient plate is increased and the patient plate generates heat.

In this context, the present invention aims to provide an adhesive, high water content hydrogel that can be used as a patient plate of an electrosurgical unit through which high current flows and that does not cause a heat generation problem even when high current flows therethrough. The present invention also aims to provide an adhesive, high water content hydrogel which provides appropriate adhesion even when attached to the skin of a human body. The present invention furthermore aims to provide an electrode pad including such an adhesive, high water content hydrogel and a composition for producing such an adhesive, high, water content hydrogel.

Solution to Problem

Specifically, the present invention provides an adhesive, high water content hydrogel that contains: a polymer matrix including a copolymer of a polymerizable monomer and a crosslinkable monomer; water; a polyhydric alcohol; an electrolyte; polyacrylic acid; and polyvinyl alcohol,
the hydrogel containing, based on 100% by weight of the total hydrogel, 40% to 70% by weight of water, 1.0% to 5.0% by weight of polyacrylic acid, and 0.5% to 5.0% by weight of polyvinyl alcohol.

Since the hydrogel contains a polymer matrix including a copolymer of a polymerizable monomer and a crosslinkable monomer; water; a polyhydric alcohol; an electrolyte; polyacrylic acid; and polyvinyl alcohol, the hydrogel can be used in various applications, for example, various types of electrode pads such as patient plates of electrosurgical units, and adhesive tapes.

Since the amount of water is 40% to 70% by weight based on 100% by weight of the total hydrogel, the hydrogel has a higher water content and a higher thermal conductivity than usual hydrogels for medical use. An electrode pad can be formed from such a hydrogel which is less likely to become hot even when high current flows therethrough. The electrode pad, which is less likely to become hot, has reduced heat generation on the skin surface when the electrode pad is attached to the skin. Furthermore, when the amount of water is 45% to 65% by weight based on 100 parts by weight of the total hydrogel, the adhesive, high water content hydrogel is excellent in adhesion as well.

Since the hydrogel contains the water-soluble polymer polyacrylic acid in an amount of 1.0% to 5.0% by weight based on 100% by weight of the total hydrogel, the adhesive, high water content hydrogel exhibits appropriate adhesion. Due to the appropriate adhesion, the hydrogel can form an electrode pad which is less likely to come off when attached to a living body but can be easily removed after use.

Also since the hydrogel contains the water-soluble polymer polyvinyl alcohol in an amount of 0.5% to 5.0% by weight based on 100% by weight of the total hydrogel, the adhesive, high water content hydrogel has excellent cohesion and maintains the stable gel form.

When the polymer matrix is produced by copolymerization using an amphiphilic monomer as part of the polymerizable monomer thereof in an amount of 0.5% to 5.0% by weight based on 100% by weight of the total hydrogel, poorly soluble photopolymerization initiators can be dissolved in a composition (liquid mixture) for producing an adhesive, high water content hydrogel even when the water content is high, so that the amount of unreacted monomers can be reduced.

The amphiphilic monomer may be N,N-dimethyl(meth)acrylamide. The use of N,N-dimethyl(meth)acrylamide as the amphiphilic monomer allows hydrophobic photopolymerization initiators to be easily dissolved.

The electrolyte may contain sodium sulfate. The use of sodium sulfate in the electrolyte imparts required conductivity to the adhesive, high water content hydrogel. Moreover, when sodium sulfate is used but no halide is contained, the risk of corrosion of the conductive layer of the electrode pad decreases, and thus the adhesive, high water content hydrogel can be used as a reliable material for an electrode pad.

The adhesive, high water content hydrogel may have a specific resistance of 1.5 kΩ·cm or less. With a specific resistance of 1.5 kΩ·cm or less, the adhesive, high water content hydrogel has a low resistance and is less likely to become hot even when high current flows therethrough.

The peel force may be not less than 1.5 N/20 mm when the hydrogel cut to a size of 1 mm thickness×100 mm length×20 ram width is attached to a Bakelite plate and peeled from the Bakelite plate at a rate of 300 mm/min in a direction 90° to the length direction. With a peel force under these predetermined conditions of not less than 1.5 N/20 mm, the hydrogel can form an electrode pad which cannot easily come off when attached to the skin of a human body, and causes no disadvantage such as separation during the use of an electrosurgical unit.

The present invention also provides a composition for producing an adhesive, high water content hydrogel, the composition containing: a polymerizable monomer and a crosslinkable monomer to be copolymerized to form a polymer matrix; water; a polyhydric alcohol; an electrolyte; polyacrylic acid; and polyvinyl alcohol, the composition containing, based on 100% by weight of the composition, 40% to 70% by weight of water, 1.0% to 5.0% by weight of polyacrylic acid, and 0.5% to 5.0% by weight of polyvinyl alcohol. The above-described adhesive, high water content hydrogel can be readily obtained by crosslinking and curing such a composition for producing an adhesive, high water content hydrogel.

The composition for producing a hydrogel may contain an amphiphilic monomer as part of the polymerizable monomer in an amount of 0.5% to 5.0% by weight based on 100% by weight of the composition.

The present invention also provides a method for producing an adhesive, high water content hydrogel, the method including: step 1 of mixing a polymerizable monomer, a monomer, an amphiphilic monomer, water, a polyhydric alcohol, an electrolyte, polyacrylic acid, polyvinyl alcohol, and a photopolymerization initiator to prepare a composition for producing an adhesive, high water content hydrogel; and step 2 of performing a polymerization crosslinking reaction of the monomer components in the composition for producing an adhesive, high water content hydrogel, the composition containing, based on 100% by weight of the composition, 40% to 70% by weight of the water, 1.0% to 5.0% by weight of the polyacrylic acid, 0.5% to 5.0% by weight of the polyvinyl alcohol, and 0.5% to 5.0% by weight of the amphiphilic monomer. A desired adhesive, high water content hydrogel can be readily produced by this production method.

The amphiphilic monomer used in the production method may be N,N-dimethyl(meth)acrylamide. In this case, the hydrophobic photopolymerization initiator is easily dissolved, so that the amount of unreacted monomers can be reduced. Therefore, a desired adhesive, high water content hydrogel can be readily produced.

The present invention further provides an electrode pad for use as an electrode for allowing a high-frequency current to flow through a living body, the electrode pad including: a surface material; a conductive layer stacked on the surface material; and a conductive adhesive gel layer coating the conductive layer, the conductive adhesive gel layer including any of the above adhesive, high water content hydrogels.

Due to the inclusion of any of the above adhesive, high water content hydrogels, the electrode pad is less likely to become hot even when high current flows therethrough, and is less likely to come off. Moreover, the electrode pad, which is less likely to become hot, has reduced heat generation on the skin surface when the electrode pad is attached to the skin.

Advantageous Effects of Invention

The adhesive, high water content hydrogel and electrode pad of the present invention are less likely to become hot even when high current flows therethrough and can be used as a patient plate of an electrosurgical unit through which high current flows. Furthermore, they have reduced heat generation on the skin surface.

Moreover, the adhesive, high water content hydrogel and electrode pad of the present invention exhibit appropriate adhesive force and provide suitable adhesion even when attached to a human skin.

The composition for producing an adhesive, high water content hydrogel of the present invention can be used to readily produce an adhesive, high water content hydrogel which is less likely to become hot even when high current flows therethrough and that is excellent in adhesion.

DESCRIPTION OF EMBODIMENTS

The adhesive, high water content hydrogel of the present invention contains: a polymer matrix including a copolymer of a polymerizable monomer and a crosslinkable monomer; water; a polyhydric alcohol; an electrolyte; polyacrylic acid; and polyvinyl alcohol.

The components of the adhesive, high water content hydrogel will be described in detail below.

Any monomer having one polymerizable carbon-carbon double bond in the molecule can be used as the polymerizable monomer. Specific examples include: non-electrolyte acrylamide derivatives such as (meth)acrylamide, N-methyl (meth)acrylamide, N-ethyl(meth)acrylamide, N-propyl (meth)acrylamide, N,N-dimethyl(meth)acrylamide, N,N-diethyl(meth)acrylamide, and acryloylmorpholine; electrolyte acrylamide derivatives such as tert-butylacrylamide sulfonic acid (TBAS) and/or salts thereof, N,N-dimethylaminoethyl acrylamide (DMAEAA) hydrochloride, and N,N-dimethylaminopropyl acrylamide (DMAPAA) hydrochloride; electrolyte acrylic derivatives such as (meth)acrylic acid, maleic acid, itaconic acid, sulfopropyl methacrylate (SPM) and/or salts thereof, and methacryloyloxyethyl trimethylammonium chloride (QDM); non-electrolyte acrylic derivatives such as hydroxyethyl (meth)acrylate and polyethylene glycol (meth)acrylate; vinylamide derivatives such as vinylpyrrolidone, vinylacetamide, and vinylformamide; and allyl alcohol. Each of these polymerizable monomers may be used alone, or a plurality of these may be used.

The polymerizable monomer preferably includes at least an amphiphilic monomer. An amphiphilic monomer refers to a polymerizable monomer soluble both in water and in a solvent (non-aqueous solvent) which is not miscible with water.

The amphiphilic monomer used in the present invention may suitably be a monomer represented by Formula (I) or Formula (II) below. Among these, the monomer represented by Formula (I) is preferred.

$$\text{(I)}\quad H_2C=C\begin{matrix}R^{11}\\ \\ C-N\begin{matrix}R^{12}\\ \\R^{13}\end{matrix}\\ \|\\O\end{matrix}$$

In the formula, $R^{11}$ represents a hydrogen atom or a methyl group; and $R^{12}$ and $R^{13}$ are the same as or different from one another and each represent a hydrogen atom or a hydrocarbon group optionally containing a heteroatom, and $R^{12}$ and $R^{13}$ may form a ring with the nitrogen atom.

Examples of the hydrocarbon group optionally containing a heteroatom as $R^{12}$ or $R^{13}$ include saturated or unsaturated monovalent groups. In the case of a monovalent, hydrocarbon group optionally containing a heteroatom, $R^{12}$ and $R^{13}$ each preferably have 1 to 10 carbon atoms, more preferably 1 to 6 carbon atoms, still more preferably 1 to 3 carbon atoms. The hydrocarbon group may be linear, branched, or cyclic, and may be, for example, an alkyl, alkenyl, or cycloalkyl group optionally containing a heteroatom.

In the case where $R^{12}$ and $R^{13}$ form a ring with the nitrogen atom to which they are attached, $R^{12}$ and $R^{13}$ together form a divalent hydrocarbon group optionally containing a heteroatom. The divalent hydrocarbon group optionally containing a heteroatom preferably has 3 to 12 carbon atoms, more preferably 3 to 10 carbon atoms, still more preferably 3 to 6 carbon atoms. The hydrocarbon group may be linear, branched, or cyclic, and may be, for example, an alkylene, alkenylene, or cycloalkylene group optionally containing a heteroatom.

The heteroatom in $R^{12}$ or $R^{13}$ is not particularly limited, and examples include oxygen and sulfur.

The monomer represented by Formula (I) is preferably one in which $R^{12}$ and $R^{13}$ are each an alkyl group optionally containing a heteroatom, more preferably a C1-C3 alkyl group.

$$\text{(II)}\quad H_2C=C\begin{matrix}R^{21}\\ \\N\begin{matrix}R^{22}\\ \\ \end{matrix}\\ C\\ \|\\O\end{matrix}$$

In the formula, $R^{21}$ represents a hydrogen atom or a methyl group; and $R^{22}$ represents a divalent hydrocarbon group optionally containing a heteroatom.

The divalent hydrocarbon group optionally containing a heteroatom as $R^{22}$ may be saturated or unsaturated. $R^{22}$ preferably has 3 to 12 carbon atoms, more preferably 3 to 10 carbon atoms, still more preferably 3 to 6 carbon atoms. The hydrocarbon group may be linear, branched, or cyclic, and may be, for example, an alkylene, alkenylene, or cycloalkylene group optionally containing a heteroatom.

The heteroatom in $R^{22}$ is not particularly limited, and examples include oxygen and sulfur.

The monomer represented by Formula (II) is preferably one in which $R^{22}$ is an alkylene group optionally containing a heteroatom, more preferably a C3-C6 alkylene group.

Specific examples of the amphiphilic monomer include N-ethyl(meth)acrylamide, N-isopropyl(meth)acrylamide, N-n-propyl(meth)acrylamide, N-cyclopropyl(meth)acrylamide, N-methyl-N-ethyl(meth)acrylamide, N,N-dimethyl(meth)acrylamide, N,N-diethyl(meth)acrylamide, N-methyl-N-isopropyl(meth)acrylamide, and N-methyl-N-n-propyl(meth)acrylamide; N-vinylpyrrolidone, N-vinylcaprolactam, N-isopropenylpyrrolidone, and N-isopropenylcaprolactam; N-(meth)acryloylpyrrolidine, and N-(meth)acryloylpiperidine; N-1-(methoxymethyl)propyl(meth)acrylamide, N-2-methoxyethyl-N-(meth)acrylamide, N-2-ethoxyethyl(meth)acrylamide, N-3-methoxypropyl(meth)acrylamide, N-3-ethoxypropyl(meth)acrylamide, N-3-isopropoxypropyl(meth)acrylamide, N-1-methyl-2-methoxyethyl(meth)acrylamide, N-2-methoxyethyl-N-n-propyl(meth)acrylamide, N-2-methoxyethyl-N-isopropyl(meth)acrylamide, N,N-di(2-methoxyethyl)(meth)acrylamide; N-tetrahydrofurfuryl(meth)acrylamide, and N-(1,3-dioxolan-2-ylmethyl)-N-(meth)acrylamide. Among these, N,N-dimethyl(meth)acrylamide is preferred.

The amount of the amphiphilic monomer is preferably 0.5% to 5.0% by weight based on 100% by weight of the total gel. When the amount is less than 0.5% by weight, the photopolymerization initiator to be added in the preparation of a composition for producing an adhesive, high water content hydrogel (hereinafter, also referred to as "pre-gelation liquid mixture" or simply as "liquid mixture") may not be dissolved, so that the gelation cannot sufficiently proceed. Also, when the amount is more than 5.0% by weight, the resulting gel may become softer so that it can be broken. The amount is more preferably 1.0% to 3.0% by weight.

Any monomer having two or more polymerizable carbon-carbon double bonds in the molecule can be used as the crosslinkable monomer. Specific examples include polyfunctional (meth)acrylamides and polyfunctional (meth)acrylates, such as N,N'-methylenebis(meth)acrylamide, N,N'-ethylenebis(meth)acrylamide, (poly)ethylene glycol di(meth)acrylate, glycerol tri(meth)acrylate, polyethylene glycol di(meth)acrylate, polypropylene glycol di(meth)acrylate, polyglycerol di(meth)acrylate, trimethylolpropane triacrylate, and pentaerythritol triacrylate. Each of these crosslinkable monomers may be used alone, or a plurality of these may be used.

The combined percentage (monomer content) of the polymerizable monomer and the crosslinkable monomer is preferably 10% to 70% by weight, more preferably 10% to 50% by weight, based on 100% by weight of the total components of the hydrogel excluding water.

With regard to the ratio of the polymerizable monomer and the crosslinkable monomer, the ratio of the crosslinkable monomer relative to 100% by weight of the polymerizable monomer is preferably 0.01% to 0.5% by weight, more preferably 0.05% to 0.25% by weight. The ratio of the crosslinkable monomer is preferably 0.01% by weight or more for shape stability. Also, the ratio of the crosslinkable monomer is preferably 0.5% by weight or less because a hydrogel having flexibility to an extent that does not impair the shape retention properties is more likely to exhibit initial tack when used as a pressure-sensitive adhesive.

The composition for producing an adhesive, high water content hydrogel may contain the components either in one pack or two packs.

The adhesive, high water content hydrogel contains at least two types of water-soluble polymers, and one of them is polyacrylic acid. This is because the addition of polyacrylic acid imparts required adhesion to the hydrogel.

The amount of polyacrylic acid to be added is 1.0% to 5.0% by weight based on 100% by weight of the hydrogel. When the amount is less than 1.0% by weight, the hydrogel has a weak adhesive force, and when formed into an electrode pad it poorly adheres to a living body and may come off during use. When the amount is more than 5.0% by weight, the pre-gelation liquid mixture has too high a viscosity and is difficult to handle. However, for use as an electrode pad, in view of adhesion to a conductive layer made of a metal such as aluminum, the amount of polyacrylic acid is more preferably 3.0% by weight or more The other type of water-soluble polymer is polyvinyl alcohol. The addition of polyvinyl alcohol imparts appropriate cohesion to the hydrogel.

The polyvinyl alcohol preferably consists of a linear polymer. This is because the mechanical strength can be readily improved by a solution of such polyvinyl alcohol in water retained in the polymer matrix.

The amount of polyvinyl alcohol to be added is 0.5% to 5.0% by weight based on 100% by weight of the hydrogel. When the amount is less than 0.5% by weight, the hydrogel may have poor cohesion and reduced adhesive force. Also, when the amount is more than 5.0% by weight, the polyvinyl alcohol is poorly soluble in the preparation of the pre-gelation liquid mixture, making it difficult to produce a desired hydrogel.

The degree of polymerization of the polyvinyl alcohol is preferably 500 to 3,000 in terms of viscosity average degree of polymerization. When the degree of polymerization is less than 500, the effect of improving mechanical strength may not be readily obtained. When the degree of polymerization is more than 3,000, the viscosity of the pre-gelation liquid mixture may greatly increase so that a uniform liquid mixture cannot be formed.

The degree of saponification of the polyvinyl alcohol is preferably 80% to 98%. When the degree of saponification is less than 80%, the solubility of polyvinyl alcohol is improved in the preparation of the liquid mixture; however, the resulting hydrogel may be less stable. Conversely, when the degree of saponification is more than 98%, the solubility may extremely decrease, possibly making it difficult to form the liquid mixture.

Examples of usable polyhydric alcohols include diols such as ethylene glycol, propylene glycol, and butanediol; polyhydric alcohols such as glycerol, pentaerythritol, and sorbitol; polyhydric alcohol condensates such as polyethylene glycol, polypropylene glycol, diglycerol, and polyglycerol; and modified polyhydric alcohols such as polyoxyethylene glycerol. Each of these polyhydric alcohols may be used alone, or a plurality of these may be used.

Of these polyhydric alcohols, it is preferable to use polyhydric alcohols which are liquid in a temperature range in which the hydrogel is actually used (for example, about 20° C. when the hydrogel is used indoor).

The amount of the polyhydric alcohol is preferably 20% to 80% by weight, more preferably 30% to 60% by weight, based or 100% by weight of the total components of the hydrogel excluding water. This is because when the amount of the polyhydric alcohol falls within the range indicated above, the change in physical properties of the resulting hydrogel due to drying is small, so that high adhesive force can be obtained.

Examples of the electrolyte added to increase the conductivity of the hydrogel include acid or mineral acid salts such as carbonates, sulfates, or phosphates, organic salts, and ammonium salts of alkali, metals (e.g. lithium, sodium, potassium) or alkaline earth metals (e.g. magnesium, calcium), excluding halides. For use as an electrode pad or the like, neutral to weakly acidic electrolytes are preferred among these.

In the case of the hydrogel used as an electrode pad, the inclusion of no halogen reduces as much as possible the risk of corrosion of the conductive layer made of a metal such as aluminum. For this reason, sodium sulfate is one of preferred examples of the electrolyte.

In the case of the hydrogel used as an electrode pad, since lower impedance is required, the amount of the electrolyte is preferably 0.1% to 10% by weight, more preferably 2% to 8% by weight, based on 100% by weight of the total components of the hydrogel excluding water. When the amount is more than 10% by weight, the electrolyte may be poorly dissolved in the liquid mixture for producing the gel. When the amount is less than 0.1% by weight, the resistance may increase when the hydrogel is dried, for example.

The water content is 40% to 70% by weight, preferably 50% to 65% by weight, based on 100% by weight of the hydrogel. The higher the water content is, the less the temperature of the hydrogel is expected to increase in the use as an electrode pad. However, the water content of more than 70% by weight can easily cause problems such as water leakage or reduced adhesion due to too high water content. When the water content is less than 40% by weight, the hydrogel when used as a patient plate may be hot if a patient plate is obtained that is less likely to become hot, the patient plate attached to the skin has reduced heat generation on the skin surface.

The pre-gelation liquid mixture usually contains a photopolymerization initiator.

Photopolymerization initiators which are cleaved by ultraviolet radiation or visible light to generate radicals are suitable, and examples include α-hydroxyketones, α-aminoketones, benzyl methyl ketals, bisacylphosphine oxides, and metallocenes. Specific examples include 2-hydroxy-2-methyl-1-phenyl-propan-1-one (trade name: Darocur 1173 available from Ciba Specialty Chemicals), 1-hydroxy-cyclohexyl-phenyl-ketone (trade name: Irgacure 184 available from Ciba Specialty Chemicals), 1-[4-(2-hydroxyethoxy)-phenyl]-2-hydroxy-2-methyl-propan-1-one (trade name: Irgacure 2959 available from Ciba Specialty Chemicals) 2-methyl-1-[(methylthio)phenyl]-2-morpholinopropan-1-one (trade name: Irgacure 907 available from Ciba Specialty Chemicals), 2-benzyl-2-dimethylamino-1-(4-morpholinophenyl)-butan-1-one (trade name: Irgacure 369 available from Ciba Specialty Chemicals), and 2-hydroxy-1-{4-[4-(2-hydroxy-2-methyl-propionyl)benzyl]phenyl}-2-methyl-propan-1-one (trade name: Irgacure 127 available from Ciba Specialty Chemicals). Each of these may be used alone, or a plurality of these may be used in combination.

The photopolymerization initiator used in the present invention is preferably a compound which is dissolved at 25° C. in an amount of 5 parts by weight or more per 100 parts by weight of the amphiphilic monomer contained in the pre-gelation liquid mixture. Such a photopolymerization initiator has increased compatibility with the amphiphilic monomer and is sufficiently dissolved even when the water content is high. As a result, the amount of unreacted monomers in the copolymerization decreases, so that a desired hydrogel can be produced. It is more preferably a compound which is dissolved in an amount of 10 parts by weight or more, still more preferably 50 parts by weight or more.

Of the particular photopolymerization initiators listed above, Irgacure 127 or Irgacure 2959 is preferred as they are well compatible with the amphiphilic monomer, and particularly with N,N-dimethyl(meth)acrylamide, although non-aqueous photopolymerization initiators are not easily dissolved in the pre-gelation liquid mixture having a high water content.

In order to sufficiently perform the polymerization reaction to reduce the amount of residual monomers, the photopolymerization initiator is added preferably in an amount of 0.01% by weight or more based on 100% by weight of the pre-gelation liquid mixture, in order to prevent discoloration (yellowing) or odor generation due to the reaction residues of the photopolymerization initiator, the amount is preferably 1.0% by weight or less, more preferably 0.05 to 0.5% by weight.

The pre-gelation liquid mixture may contain a pH adjuster. This is because excessively acidic pH conditions may cause corrosion of the conductive layer in the use as an electrode pad. In order to adjust the pH, for example, citric acid or sodium citrate may be added.

The hydrogel may contain other additives as needed. Examples of other additives include antiseptic agents, disinfectants, antifugal agents, rust preventive agents, antioxidants, defoaming agents, stabilizers, perfumes, surfactants, colorants, and medicinal ingredients (for example, anti-inflammatory agents, vitamins, skin-whitening agents).

A method for producing the adhesive, high water content hydrogel will be described below. The adhesive, high water content hydrogel can be produced by mixing and stirring the predetermined components to prepare a composition for producing an adhesive, high water content hydrogel, and performing a polymerization crosslinking reaction of the composition while simultaneously forming the product into a given shape.

For example, the adhesive, high water content hydrogel can be produced by a method including: step 1 of mixing a polymerizable monomer, a crosslinkable monomer, an amphiphilic monomer, water, a polyhydric alcohol, an electrolyte, polyacrylic acid, polyvinyl alcohol, and a photopolymerization initiator to prepare a composition for producing an adhesive, high water content hydrogel; and step 2 of performing a polymerization crosslinking reaction of the monomer components in the composition for producing an adhesive, high water content hydrogel, wherein predetermined amounts of the water, the polyacrylic acid, the polyvinyl alcohol, and the amphiphilic monomer are incorporated.

Specifically, the pre-gelation liquid mixture can be prepared by firstly dissolving the photopolymerization initiator in the amphiphilic monomer, and mixing and stirring the resulting amphiphilic monomer and the polymerizable monomer, crosslinkable monomer, water, polyhydric alcohol, electrolyte, polyacrylic acid, polyvinyl alcohol, and other components to dissolve them without leaving solid residues.

The liquid mixture thus prepared is, for example, injected into a frame, followed by a polymerization crosslinking reaction of the monomer components contained therein to form a polymer matrix including a copolymer of the polymerizable monomer and the crosslinkable monomer, whereby an adhesive, high water content hydrogel of a desired shape can be obtained. Alternatively, the liquid mixture is poured between a surface material and a cover film and then subjected to a polymerization crosslinking reaction while maintaining a constant thickness to obtain a sheet of an adhesive, high water content hydrogel. Still alternatively, a surface material or a cover film is thinly coated with the liquid mixture, followed by a polymerization crosslinking reaction to obtain a thinner film of an adhesive, high water content hydrogel.

In the case where the polymerization/crosslinking is carried out by irradiation with ultraviolet radiation, the cumulative dose of radiation to the liquid mixture is preferably 1,000 mJ/cm$^2$ or more. The cumulative radiation dose of 1,000 mJ/cm$^2$ or more is enough for sufficiently promoting the polymerization reaction. A cumulative radiation dose of 2,000 mJ/cm$^2$ or more is more preferred because this can reduce the amount of residual monomers in the hydrogel to 100 ppm or less. The upper limit of the cumulative radiation dose is not necessarily limited, and any radiation dose that allows the polymerization reaction to sufficiently proceed is enough. However, since excessive irradiation may cause disadvantages such as an increase in size of the system, the use of excess energy, or the need for removal of generated heat, it is desirable to minimize the radiation dose.

The adhesive, high water content hydrogel produced as above keeps safety for and adhesion to the skin, and also can be easily provided with conductivity due to the added electrolyte and the high water content. Therefore, the hydrogel can be suitably used as an adhesive conductive member such as an electrode pad.

The following describes an example of the adhesive, high water content hydrogel used as an electrode pad (patient plate) of an electrosurgical unit.

Figure 1:
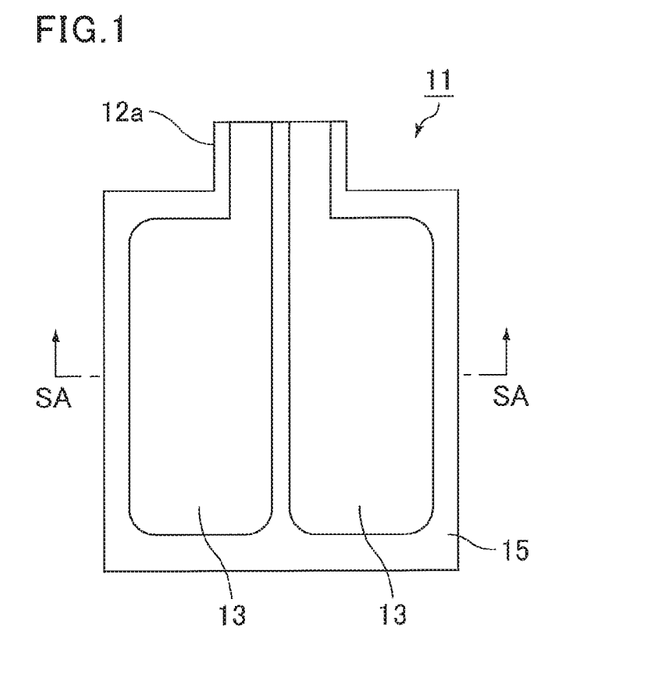
FIG. 1 illustrates a plan view of an electrode pad.
Figure 2:
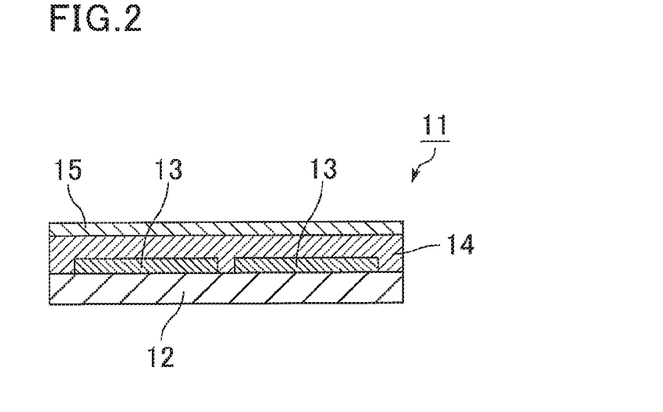
FIG. 2 illustrates an SA-SA line cross-sectional view of the electrode pad in FIG. 1.

FIG. 1 illustrates a plan view of an electrode pad 11. FIG. 2 illustrates an SA-SA line cross-sectional view of FIG. 1. As shown in FIG. 1, the electrode pad 11 includes a surface material 12 having a substantially tetragonal plain shape with a tongue piece 12a at one side thereof, conductive layers 13 provided on the surface material 12 as shown in FIG. 2, and an adhesive, high water content hydrogel 14 stacked on members. The surface of the adhesive, high water content hydrogel 14 is covered with a cover film 15.

The surface material 12 may be formed of a resin film having both shape retention properties and flexibility, such as non-conductive films, e.g. polyethylene terephthalate films, polypropylene films, or polyethylene films, paper, nonwoven fabrics, and foam sheets. The surface material 12 may have a decorative print thereon to improve the appearance as an electrode pad.

In view of handleability, the thickness of the surface material 12 is suitably about 10 to 200 μm.

The conductive layers 13 are each integrally stacked on the surface material 12 in areas excluding the peripheral rim. They are connectable to lead wires through the tongue piece 12a.

The conductive layers 13 may be formed of any material which is flexible enough to chance its shape along the surface of a living body and has low electrical resistance. Examples include metal foils such as aluminum foil, stainless steel foil, copper foil, and nickel foil; and composite films obtained by adhering a layer of a conductive material such as carbon, silver, or silver chloride to a synthetic resin film via a synthetic resin binder or other binders. Among these, metal foils are preferred in view of conductivity, with aluminum foil being more preferred in view of lightness, cost, safety, processability, and other aspects.

The thickness of the conductive layers 13 is preferably 5 to 50 μm because too thick conductive layers 13 have less flexibility and may not allow the electrode pad 11 to change the shape along a living body, while too thin conductive layers 13 may result in reduced mechanical strength.

The conductive layers 13 can be integrally stacked on the surface material 12 by laminating the conductive layers 13 to the surface material 12, or alternatively by integration using an adhesive or the like or by applying a layer of a resin coating liquid onto the conductive layers 13.

The adhesive, high water content hydrogel 14 coating the conductive layers 13 is the above-described hydrogel characterized by having both high water content and adhesion to the skin. The adhesive, high water content hydrogel 14 can be formed by applying the pre-gelation liquid mixture onto the surface material 12 on which the conductive layers 13 are stacked, followed by a crosslinking reaction. It can also be formed by stacking the surface material 12 and the adhesive, high water content hydrogel 14 formed separately as a coating film on a resin film.

The thickness of the adhesive, high water content hydrogel 14 is preferably 0.5 to 1.2 mm. A thickness of less than 0.5 mm is too small, so that the hydrogel may become hot due to the high-frequency current of an electrosurgical unit. A thickness of more than 1.2 mm will not produce an additional effect of the electrode pad 11, thereby wasting material costs.

A cover film 15 is further provided on the adhesive, high water content hydrogel 14 to cover the adhesive, high water content hydrogel 14 so that the adhesive, high water content hydrogel 14 is protected and prevented from drying. The cover film 15 is released before the use of the electrode pad 11, and the adhesive, high water content hydrogel 14 side is attached to the human skin.

The electrode pad 11 thus formed has a low specific resistance of 0.1 to 3.0 kΩ·cm, preferably 1.5 kΩ·cm or lower. The electrode pad 11 having a low specific resistance can be used as, for example, a patient plate of an electrosurgical unit. The electrode pad 11 having a specific resistance of 1.5 kΩ·cm or lower can be used as a safe patient plate whose temperature will not unnecessarily rise even when high current flows therethrough and thus does not cause problems such as low-temperature burns. Furthermore, such an electrode pad 11 has adhesion to living bodies so that it does not easily come off but is not difficult to remove.

In addition to the use as patient plates of electrosurgical units, the electrode pad 11 can also be used as electrodes of high-frequency therapeutic apparatuses, for example. Thus, it can be widely used as earth electrodes or sensing electrodes of therapeutic, monitoring, or other devices using high-frequency current.

In addition to electrode pads, the adhesive, high water content hydrogel can be suitably used in surgical tapes to be attached to living bodies, and tapes for fixing catheters, drip tubes, or sensors; compresses, wound dressings, pressure-sensitive adhesives to be attached to living bodies; and industrial pressure-sensitive adhesives for building materials, electronic materials, and other materials.

EXAMPLES

The present invention will be further described with reference to, but not limited to, examples below.

Hydrogel samples obtained in the examples and comparative examples were measured for their adhesive force and specific resistance as specifically described below.

Examples, Reference Examples, Comparative Examples

Pre-gelation liquid mixtures of the examples and comparative examples were prepared by mixing the components mentioned below based on the formulations (parts by weight) shown in Tables 1 and 2, and dissolving and stirring the mixture. The components used are: acrylamide (AAM) and N,N-dimethylacrylamide (DMAA, amphiphilic monomer) as polymerizable monomers; N,N'-methylenebisacrylamide (MBAA) as crosslinkable monomer; glycerol as a polyhydric alcohol; polyacrylic acid (PAA) and polyvinyl alcohol (PVA, degree of saponification: 88%, trade name: VP-18 available from Japan Vam & Poval Co., Ltd) as water-soluble polymers; sodium sulfate as an electrolyte; Irgacure 2959 (trade name: IR2959 available from Ciba Specialty Chemicals, solubility per 100 parts by weight of N,N-dimethylacrylamide at 25° C.: 80 parts by weight), Irgacure 127 (trade name: IR127 available from Ciba Specialty Chemicals, solubility per 100 parts by weight of N,N-dimethylacrylamide at 25° C.: 120 parts by weight), and Irgacure 184 (trade name: IR184 available from Ciba Specialty Chemicals, solubility per 100 parts by weight of N,N-dimethylacrylamide at 25° C.: 330 parts by weight) as photopolymerization initiators; citric acid and sodium citrate as optional additives; and water as a solvent.

Next, each pre-gelation liquid mixture (liquid form) was dropped on a 100 µm-thick polyethylene terephthalate film (cover film) having an exposed face coated with silicone. Then, a silicone-coated polyethylene terephthalate film (another film) having a thickness of 40 µm was prepared, and the silicone-coated face of this film was applied to the dropped pre-gelation liquid mixture to cover the liquid mixture. After that, these films between which the pre-gelation liquid mixture was sandwiched were allowed to pass through a 0.84 mm gap to press and spread the pre-gelation liquid mixture, followed by irradiation with ultraviolet radiation for 60 seconds by a metal halide lamp to cure the pre-gelation liquid mixture (cumulative radiation dose: 3,000 mJ/cm$^2$). Subsequently, the 40 µm-thick polyethylene terephthalate film was released and replaced by a silicone-coated polyethylene film having a thickness of 40 µm. In this manner, hydrogel samples of Examples 1 to 8, Reference Example 2, and Comparative Examples 1 to 2, 4, and 6 to 8 made from the raw materials shown in Table 1 and 2 and having both flat surfaces covered with the polyethylene terephthalate film and the polyethylene film were prepared. The pre-gelation liquid mixtures of Reference Example 1 and Comparative Examples 3 and 5 were not subjected to the preparation of hydrogel samples because of their poor solubility.

TABLE 1

|  |  | Example | | | | |
|---|---|---|---|---|---|---|
|  |  | 1 | 2 | 3 | 4 | 5 |
| Formulation (parts by weight) | AAM | 18 | 18 | 18 | 18 | 15 |
|  | DMAA | 1 | 1 | 1 | 1 | 5 |
|  | MBAA | 0.0324 | 0.0324 | 0.0324 | 0.0324 | 0.0324 |
|  | Water | 40 | 50 | 60 | 60 | 60 |
|  | Na$_2$SO$_4$ | 0.5 | 0.5 | 0.5 | 0.5 | 0.5 |
|  | IR127 | 0.1 | 0.1 | 0.1 | 0.1 | 0.1 |
|  | IR184 | 0 | 0 | 0 | 0 | 0 |
|  | IR2959 | 0.05 | 0.05 | 0.05 | 0.05 | 0.05 |

TABLE 1-continued

|  |  |  |  |  |  |  |
|---|---|---|---|---|---|---|
|  | PAA | 3 | 3 | 3 | 5 | 3 |
|  | PVA | 2 | 2 | 2 | 2 | 2 |
|  | Citric acid | 0.2 | 0.2 | 0.2 | 0 | 0 |
|  | Na citrate | 2.5 | 2.5 | 2.5 | 4 | 2.5 |
|  | Glycerol | balance | balance | balance | balance | balance |
|  | Total | 100 | 100 | 100 | 100 | 100 |
| Properties | Solubility of liquid mixture | good | good | good | good | good |
|  | 90° adhesion  N/20 mm | 3.2 | 2.7 | 2.7 | 3.1 | 1.9 |
|  | Specific resistance  kΩ · cm | 0.74 | 0.38 | 0.32 | 0.32 | 0.33 |
|  | Heat generation temperature  °C. | 9.1 | 8.7 | 7.5 | 7.8 | 8.3 |
|  | Al adhesion  N/20 mm | 3.4 | 3.2 | 2.2 | 3.1 | 1.5 |

|  |  | Example | | | Reference Example | |
|---|---|---|---|---|---|---|
|  |  | 6 | 7 | 8 | 1 | 2 |
| Formulation (parts by weight) | AAM | 18 | 19 | 16 | 19 | 11.5 |
|  | DMAA | 1 | 0 | 1 | 0 | 10 |
|  | MBAA | 0.0324 | 0.0324 | 0.0288 | 0.0324 | 0.0324 |
|  | Water | 70 | 60 | 60 | 60 | 60 |
|  | Na$_2$SO$_4$ | 0.5 | 0.5 | 0.5 | 0.5 | 0.5 |
|  | IR127 | 0.1 | 0 | 0 | 0.1 | 0.1 |
|  | IR184 | 0 | 0 | 0.1 | 0 | 0 |
|  | IR2959 | 0.05 | 0.15 | 0.07 | 0.05 | 0.05 |
|  | PAA | 3 | 3 | 3 | 3 | 3 |
|  | PVA | 2 | 2 | 2 | 2 | 2 |
|  | Citric acid | 0 | 0.2 | 0.2 | 0.2 | 0.2 |
|  | Na citrate | 2.5 | 2.5 | 1.8 | 2.5 | 2.5 |
|  | Glycerol | balance | balance | balance | balance | balance |
|  | Total | 100 | 100 | 100 | 100 | 100 |
| Properties | Solubility of liquid mixture | good | good | good | poor | good |
|  | 90° adhesion  N/20 mm | 1.5 | 2.5 | 3.0 | — | fragile |
|  | Specific resistance  kΩ · cm | 0.23 | 0.33 | 0.39 | — | — |
|  | Heat generation temperature  °C. | 7.1 | 7.7 | 8.1 | — | — |
|  | Al adhesion  N/20 mm | 1.5 | 2.0 | 1.5 | — | — |

TABLE 2

|  |  | Comparative Example | | | | | | | |
|---|---|---|---|---|---|---|---|---|---|
|  |  | 1 | 2 | 3 | 4 | 5 | 6 | 7 | 8 |
| Formulation (parts by weight) | AAM | 18 | 18 | 18 | 18 | 18 | 18 | 15 | 13 |
|  | DMAA | 1 | 1 | 1 | 1 | 1 | 1 | 1 | 1 |
|  | MBAA | 0.0324 | 0.0324 | 0.0324 | 0.0324 | 0.0324 | 0.0324 | 0.0324 | 0.04 |
|  | Water | 20 | 60 | 60 | 60 | 60 | 60 | 75 | 80 |
|  | Na$_2$SO$_4$ | 0.5 | 0.5 | 0.5 | 0.5 | 0.5 | 0.5 | 0.5 | 0.5 |
|  | IR127 | 0 | 0.1 | 0.1 | 0.1 | 0.1 | 0.1 | 0.1 | 0.1 |
|  | IR184 | 0 | 0 | 0 | 0 | 0 | 0 | 0 | 0 |
|  | IR2959 | 0.15 | 0.05 | 0.05 | 0.05 | 0.05 | 0.05 | 0.05 | 0.05 |
|  | PAA | 3 | 0.5 | 10 | 3 | 3 | 0 | 3 | 1 |
|  | PVA | 2 | 2 | 2 | 0 | 6 | 2 | 2 | 1 |
|  | Citric acid | 0.2 | 0 | 0 | 0.2 | 0.2 | 0.2 | 0.2 | 0.2 |
|  | Na citrate | 2.5 | 2 | 6.5 | 2.5 | 2.5 | 2.5 | 2.5 | 2.5 |
|  | Glycerol | balance | balance | balance | balance | balance | balance | balance | balance |
|  | Total | 100 | 100 | 100 | 100 | 100 | 100 | 100 | 100 |
| Properties | Solubility of liquid mixture | good | good | poor | good | poor | good | good | good |
|  | 90° adhesion  N/20 mm | 4.7 | 1.6 | — | 1.4 | — | 0.57 | 0.74 | fragile |
|  | Specific resistance  kΩ · cm | 3.76 | 0.35 | — | 0.35 | — | 0.34 | 0.22 | — |

TABLE 2-continued

| | | Comparative Example | | | | | | | |
|---|---|---|---|---|---|---|---|---|---|
| | | 1 | 2 | 3 | 4 | 5 | 6 | 7 | 8 |
| Heat generation temperature | °C. | 12.7 | 8.0 | — | 8.1 | — | 8.4 | 7.0 | — |
| Al adhesion | N/20 mm | 3.9 | 0.93 | — | 1.4 | — | 0.61 | 0.81 | — |

Tables 1 and 2 show the characteristics of the liquid mixtures or hydrogel samples of the examples, reference examples, and comparative examples together with test results. The symbol "-" in the tables indicates no test performed.

<Aptitude of Liquid Mixture>

In the row titled "Solubility of liquid mixture" in Tables 1 and 2, "good" indicates that the components of the obtained liquid mixture were dissolved without leaving solid residues, while "poor" indicates that the liquid mixture had problems such as turbidity or a difficulty in application due to excessively high viscosity.

<90° Adhesive Force Measurement>

The 90° adhesive force measurements are displayed in the row titled "90° adhesion" in Tables 1 and 2.

Specifically, the test was carried out as follows: Each sample (hydrogel sample) was cut into a 20-100 mm rectangular strip. Then, the polyethylene film was released and a backing material was attached thereto. After that, the cover film was released, and the sample having a thickness of 1 mm, a length of 100 mm, and a width of 20 mm was attached to a Bakelite plate. After a 2 kg roller was moved back and forth once on the sample, the sample was set on a TENSION (available from Orientec). Then, the peel force when the sample was peeled at a rate of 300 mm/min in a direction 90° to the length direction (0°) of the sample in accordance with JIS-Z 0237 was measured and taken as the adhesive force.

<Measurement of Specific Resistance>

The specific resistance measurements are displayed in the row titled "Specific resistance" in Tables 1 and 2.

Each sample (hydrogel sample) was cut into a 20 mm×20 mm square, and stainless steel plates were attached to the respective faces of the sample piece. The impedance when a 1 kHz, 10 mA current was passed between the stainless steel plates was measured. The specific resistance was calculated from the measured impedance (I) and the area (S) and thickness (d) of the sample piece using the following equation.

Specific resistance (Ω·cm)=$I(\Omega)/d$ (cm)×$S(cm^2)$

<Heat Generation Temperature>

Each hydrogel sample was measured for heat generation temperature when it was used as a patient plate (electrode pad) of an electrosurgical unit. The results are displayed in the row titled "Heat generation temperature" in Tables 1 and 2.

Specifically, the test was as follows: The polyethylene film was released from each sample (hydrogel sample). A conductive layer consisting of a laminate of an aluminum foil (9 μm) and a PET film was prepared, and the aluminum foil side of the conductive layer was applied to the hydrogel, followed by attaching a surface material layer (with adhesive on one side) to the top of the resulting laminate. Then, the stack was punched out into a 109 $cm^2$ rectangular shape to prepare a test patient plate. Two patient plates thus prepared were attached to the subject's back, and another piece thereof was attached to the inner thigh where hairs were shaved in advance. Assuming the use for an electrosurgical unit, a 1.5 A current was allowed to flow from the patient plates attached to the back for 1 minute, and the current was collected at the patient plate attached to the thigh. Then, the patient plate on the inner thigh was removed, and the skin surface temperature in the area where the patient plate had been attached was determined by thermography. The skin temperature in the same area before the test was also determined by thermography. The skin temperature before the test was subtracted from the highest skin heat generation temperature of the captured image, and this difference is taken as the heat generation temperature.

<Adhesion to Aluminum Foil>

The adhesion of the adhesive, high water content hydrogel to an aluminum foil as a conductive layer was measured. The results are displayed in the row titled "Al adhesion" in Tables 1 and 2.

Specifically, the test was carried out as follows: Each sample (hydrogel sample) was cut into a 20-100 mm rectangular strip. Then, the polyethylene film was released and an Al film was attached thereto. A 2 kg roller was moved back and forth once on the resulting laminate so that the adhesive, high water content hydrogel was adhered to the Al film, followed by standing still at room temperature for two days. Thereafter, the cover film was released and a backing material was attached to the exposed adhesive, high water content hydrogel surface. Separately, the face on the Al film side was bonded to SUS with a double-sided tape. Then, an end portion of the adhesive, high water content hydrogel on the backing material was peeled from the Al film and set on a TENSION (available from Orientec) to measure the peel force when the hydrogel was peeled at a rate of 300 mm/min in the 90° direction. The measured peel force is taken as the adhesive force between Al and the gel.

In Comparative Example 1 where the water content was as low as 20 parts by weight, the heat generation temperature exceeded 10° C., thereby failing to achieve the intended goal. In Comparative Example 8 where the water content was as high as 80 parts by weight, the gel was fragile and poor in adhesion. In Comparative Example 7 where the water content was 75 parts by weight, although the heat generation temperature was reduced, slightly poor adhesion was observed, with the 90° adhesion being less than 0.98 N/20 mm.

In contrast, in Examples 1 to 8 where the water content was 40 to 70 parts by weight, the results were good in all the tests. In Example 7 where N,N-dimethylacrylamide and Irgacure 127 were not contained, residual monomers were observed and some concern about odor and skin irritation was raised.

In Reference Example 1 where the polymerizable monomer did not include N,N-dimethylacrylamide as an amphiphilic monomer, the liquid mixture was turbid supposedly due to the undissolved photopolymerization initiator. In Reference Example 2 where 10 parts by weight of N,N-dimethylacrylamide was added, the hydrogel was fragile and resulted in poor adhesion.

In Comparative Example 6 where no polyacrylic acid was added, considerably low adhesion was observed. In Comparative Example 3 where 10 parts by weight of polyacrylic acid was added, the liquid mixture had too high a viscosity and was difficult to form into a predetermined shape. In Comparative Example 2 where 0.5 part by weight, of polyacrylic acid was added, although the adhesive, high water content hydrogel had generally excellent properties, it exhibited slightly poor adhesion to the aluminum foil.

In Comparative Example 4 where no polyvinyl alcohol was added, the hydrogel resulted in slightly poor adhesion, with the 90° adhesion being 1.4 N/20 mm, which is higher than 0.98 N/20 mm but lower than 1.5 N/20 mm. In Comparative Example 5 where 6 parts by weight of polyvinyl alcohol was added, on the other hand, the liquid mixture had too high a viscosity and was difficult to form into a predetermined shape.

The above descriptions of embodiments and examples are merely some modes of the present invention. The present invention is not limited to these modes, and includes modified modes in terms of the shape, size, material, production method, and other conditions of the members, without departing from the spirit, of the present invention.

REFERENCE SIGNS LIST

11 Electrode pad
12 Surface material
12a Tongue piece
13 Conductive layer
14 Adhesive, high water content hydrogel
15 Cover film

The invention claimed is:

1. An adhesive, high water content hydrogel, comprising:
   a polymer matrix comprising a copolymer of a polymerizable monomer and a crosslinkable monomer;
   water;
   a polyhydric alcohol;
   an electrolyte;
   polyacrylic acid; and
   only a single polyvinyl alcohol,
   the adhesive, high water content hydrogel comprising, based on 100% by weight of the total adhesive, high water content hydrogel, 55% to 70% by weight of water, 1.0% to 5.0% by weight of polyacrylic acid, and 0.5% to 2.0% by weight of polyvinyl alcohol, and
   at least one of conditions (i) or (ii) is met:
   (i) the polymer matrix is produced by copolymerization using an amphiphilic monomer as part of the polymerizable monomer in an amount of 0.5% to 5.0% by weight based on 100% by weight of the total adhesive, high water content hydrogel, wherein the amphiphilic monomer is N,N-dimethyl(meth)acrylamide, or
   (ii) the electrolyte comprises sodium sulfate.

2. The adhesive, high water content hydrogel according to claim 1, wherein condition (i) is met.

3. The adhesive, high water content hydrogel according to claim 1,
   wherein the adhesive, high water content hydrogel comprises 55% to 65% by weight of water.

4. The adhesive, high water content hydrogel according to claim 1,
   wherein the electrolyte comprises sodium sulfate.

5. The adhesive, high water content hydrogel according to claim 1,
   wherein a peel force is not less than 1.5 N/20 mm when the adhesive, high water content hydrogel cut to a size of 1 mm thickness×100 mm length×20 mm width is attached to a Bakelite plate and peeled from the Bakelite plate at a rate of 300 mm/min in a direction 90° to the length direction.

6. An adhesive, high water content hydrogel, comprising:
   a polymer matrix comprising a copolymer of a polymerizable monomer and a crosslinkable monomer;
   water;
   a polyhydric alcohol;
   an electrolyte;
   polyacrylic acid; and
   only a single polyvinyl alcohol,
   the adhesive, high water content hydrogel comprising, based on 100% by weight of the total adhesive, high water content hydrogel, 60% to 70% by weight of water, 1.0% to 5.0% by weight of polyacrylic acid, and 0.5% to 5.0% by weight of polyvinyl alcohol, and
   at least one of conditions (i) or (ii) is met:
   (i) the polymer matrix is produced by copolymerization using an amphiphilic monomer as part of the polymerizable monomer in an amount of 0.5% to 5.0% by weight based on 100% by weight of the total adhesive, high water content hydrogel, wherein the amphiphilic monomer is N,N-dimethyl(meth)acrylamide, or
   (ii) the electrolyte comprises sodium sulfate.

7. The adhesive, high water content hydrogel according to claim 6, wherein condition (i) is met.

8. The adhesive, high water content hydrogel according to claim 6,
   wherein the adhesive, high water content hydrogel comprises 60% to 65% by weight of water.

9. The adhesive, high water content hydrogel according to claim 6,
   wherein the electrolyte comprises sodium sulfate.

10. The adhesive, high water content hydrogel according to claim 6,
    wherein a peel force is not less than 1.5 N/20 mm when the adhesive, high water content hydrogel cut to a size of 1 mm thickness×100 mm length×20 mm width is attached to a Bakelite plate and peeled from the Bakelite plate at a rate of 300 mm/min in a direction 90° to the length direction.

11. An electrode pad, comprising the adhesive, high water content hydrogel according to claim 1.

12. An electrode pad, comprising the adhesive, high water content hydrogel according to claim 6.

* * * * *

UNITED STATES PATENT AND TRADEMARK OFFICE
CERTIFICATE OF CORRECTION

PATENT NO. : 11,162,006 B2
APPLICATION NO. : 15/124878
DATED : November 2, 2021
INVENTOR(S) : H. Tanaka It is certified that error appears in the above-identified patent and that said Letters Patent is hereby corrected as shown below:

In the Claims

Column 18, Line 12 (Claim 5, Line 5) please change "thickness×100 mm length×20" to
-- thickness × 100 mm length × 20 --

Column 18, Line 51 (Claim 10, Line 5) please change "thickness×100 mm length×20" to
-- thickness × 100 mm length × 20 --

Signed and Sealed this
Twenty-fourth Day of May, 2022

*Katherine Kelly Vidal*

Katherine Kelly Vidal
*Director of the United States Patent and Trademark Office*